(12) United States Patent
Sannicolo' et al.

(10) Patent No.: US 6,369,260 B1
(45) Date of Patent: Apr. 9, 2002

(54) PROCESS FOR THE PREPARATION OF A PHARMACOLOGICALLY ACTIVE CHEMICAL COMBINATION

(75) Inventors: Francesco Sannicolo'; Tiziana Benincori, both of Milan; Piero Del Soldato, Monza, all of (IT)

(73) Assignees: Laboratori Alchemica S.r.l., Milan (IT); Nicox SA, Valbonne-Sophia Antipolis (FR); a part interest ( * ) Notice: Subject to any disclaimer, the term of this patent is extended or adjusted under 35 U.S.C. 154(b) by 0 days.

(21) Appl. No.: 08/836,756

(22) PCT Filed: Nov. 20, 1995

(86) PCT No.: PCT/EP95/04556

§ 371 Date: May 16, 1997

§ 102(e) Date: May 16, 1997

(87) PCT Pub. No.: WO96/15809

PCT Pub. Date: May 30, 1996

(30) Foreign Application Priority Data

Nov. 22, 1994 (IT) .......................................... MI94A2362

(51) Int. Cl.$^7$ .............................................. C07C 229/00
(52) U.S. Cl. ........................................... 560/44; 560/43
(58) Field of Search ...................................... 560/43, 44

(56) References Cited

U.S. PATENT DOCUMENTS

| | | | | |
|---|---|---|---|---|
| 3,025,215 A | | 3/1962 | Gaertner et al. ............... | 167/33 |
| 4,420,490 A | * | 12/1983 | Sallmann et al. ............ | 424/309 |
| 4,704,468 A | * | 11/1987 | Zabunova et al. ............. | 560/43 |

FOREIGN PATENT DOCUMENTS

| | | |
|---|---|---|
| FR | 2.007.815 | 1/1970 |
| FR | 2.237.621 | 2/1975 |
| GB | 872.130 | 7/1961 |
| GB | 1.013.235 | 12/1965 |
| WO | WOA9109831 | 7/1991 |

OTHER PUBLICATIONS

J.Antibiot., 1992, vol. 45, No. 4, pp. 589–594.
Perrone Et Al. "Dual–action penems".
Biochemistry, 1989, vol. 28, No. 9, pp. 3886–3894.
Shen Et Al. "Mechanism of inibition of DNA gyrase . . . ".
Korean J.Med.Chem., 1992, vol. 2,No. 1, pp. 17–26.
Kim Et Al. "N–Maleylpiperazino–8–fluoro–ciprofloxacin . . . ".
Farmaco,Ediz.Scient., vol. 40, No. 5, 1985, pp. 334–346.
E.Calvi Et Al. "Sintesi e studio farmacologico di nuoviesteri . . . ".
Farmaco,Ediz.Scient.,vol. 40?No. 5, 1985,pp. 770–776.
C.Balsamini Et Al. "Saliciloilderivati del 4–amminofenolo".
Bulletin De La Soc.Chim. De France,2 Partie,No. 3/4, 1979.
M.Hauteville Et Al. "Un nuveau type de flavonoides naturels . . . ".
CA 106:175953, abstract of JP 61291554, (1986).*
CA 112:55248, abstract of DD 264820 (1989), 1986.*

* cited by examiner

Primary Examiner—Sabiha Qazi
(74) Attorney, Agent, or Firm—Collard & Roe, P.C.

(57) ABSTRACT

Process for the preparation of a pharmacologically active chemical combination constituted by the association, through chemical bonds, of units equal to one another, having each an own pharmacological activity, and with the general formula (I): M—A—X—B—M, where M indicates said unit having an own pharmacological activity, X indicates a "bidentate" structure suitable to interconnect the M units, A and B indicate functional groups either equal to or different from one another which allow the interconnection between M and X.

2 Claims, No Drawings

PROCESS FOR THE PREPARATION OF A PHARMACOLOGICALLY ACTIVE CHEMICAL COMBINATION

This application is a 371 of PCT/EP95/04556 filed on Nov. 20,1995.

This invention refers to a process for the preparation of a pharmaceutically active chemical combination constituted by the association, through chemical bonds, of two units equal to one another, having pharmacological activity.

The invention also relates to said pharmacologically active chemical combination obtained through said process, and its utilization for the preparation of pharmaceutical compositions having pharmacological activity.

The invention furtherly relates to pharmaceutical compositions comprising said chemical combination as active principle.

PRIOR ART

The researchers of the whole world have been engaged for many years in the study and development of pharmacologically active compounds, in order to obtain new drugs. Parallelly to this line of research, great importance is given also the research aiming at finding systems allowing to improve the therapeutical performances of large consumption drugs that are already marketed. Many medicines known and commonly utilized in therapy, while being provided with a good pharmacological activity, have often some drawbacks; some of these problems are due, for instance, to the fact that, often because of unsuitable hydrophilic or hydrophobic, characteristics, the drug may have a far from optimum bioavailability, which may constitute an obstacle to reach the action site, with ensuing reduction in the therapeutical activity. Furthermore, once the molecule constituting the active principle has entered the circle, it may be subjected to the activity of aspecific enzymes, which may cause adverse reactions of different nature; furthermore, the administration system of the drug may sometimes involve problems, due for instance to the chemical-physical instability of the molecule that constitute the active principle, with ensuing inactivation risks and also marked inconveniences for the patient.

As known, the systems suitable to improve the tharapeutical performances of drugs require, for instance, the use of appropriate delivery systems, based on appropriate pharmaceutical formulations which, while keeping the activity of the drug inalterated, improve its absorption, the bioavalability and make its administration easier. Other systems used for this purpose involve the preparation of prodrugs, precursor compounds, mostly pharmacologically inert, of the real drug, which are transformed into the pharmacologically active product through one or more chemical and/or enzymatic reactions. Different examples in this sense are reported in the literature, some of which have had a remarkable success from both therapeutical and commercial points of view.

A particular interpretation of the "prodrug" concept is represented, as is reported in the literature by some known products used in the inflammatory pathologies of the intestine, such as for ice Olsalazine and Sulfasalazine, whose molecular structure is derived from two phamacologically active units, either equal to or different from one another, directly bound to one another by transformation of the aninic groups of the two molecules in to an azoic type bond. Generally, the aforementioned therapeutical approaches have the drawback of supplying often non constant and non foreseeable responses during the therapy being carried on, with ensuing difficulty in the choice of the adequate therapy and possible inconveniences for the patients subjected to such therapies.

A very much felt problem in the field of pharmacological therapy is that associated to the duration of the effect reached through the administration of the drug. Usually, in fact, once administered, the drug employs a variable time, which depends on the whole of all the factors already considered (for instance, bioavailability, absorption level, stability, administration method) to reach the target; once the target has been reached, the drug exerts its activity, whose effect generally depends on the administered dose, after which it undergoes several chemical-physical changes, and is metabolized and eliminated in variable times. Because of this mechanism of activity, most drugs cannot achieve a long-lasting effect; in most cases; such effect disappears as soon as die metabolization process starts. This causes considerable inconveniences since, to obtain a longer effect, it is almost always necessary to administer drug doses at shorter intervals, with a risk of accumulation and ensuing increase in side effects.

OBJECTS OF THE INVENTION

Object of this invention is therefore to realize a process for the preparation of a pharmacologically active chemical combination allowing the controlled release of the constituent active principles once the target site has been reached.

A further object of this invention is to realize a process for the realization of a pharmacologically active chemical combination with good characteristics of bioavailability, well tolerated (often even more than he individual constituent active principle) and of easy administration Still a further object of this invention is to realize a process for the preparation of a pharmacologically active chemical combination allowing to obtain a long-lasting therapeutical effect, without recourse to a proportional increase in the frequency of the doses used.

Still another object of this invention is to provide a pharmacologically active chemical combination, realized by means of said process, as well as pharmaceutical compositions comprising as active principle said chemical combination.

DESCRIPTION OF THE INVENTION

These and still other objects and related advantages, which will be more clearly apparent from the following description, are reached by a process for the preparation of a pharmacologically active chemical combination, which, according to this invention, consists in chemically combining a first and a second unit (or radical) of molecular structures corresponding to pharmacologically active compounds, through a system having a "bidentate" structure, so as to realize a chemical combination having the following general formula:

$$M-A-X-B-M \tag{I}$$

where
  M indicates said first and second units (or radicals) of molecular structures corresponding to pharmacologically active compounds, said units (or radicals) being related down to said molecular structures by saturation of the free valences with atoms or groups of atoms such as hydrogen, OH group, OEt group;
  X indicates a "bidentate" structure, suitable to interconnect said M according to the general formula (I);

A and B are equal to or different from one another and indicate functional groups which allow said interconnection between said M and said X.
More particularly, always according to this invention, said M, equal to one another, are chosen among the following groups:
GROUP 11
(LXIV)
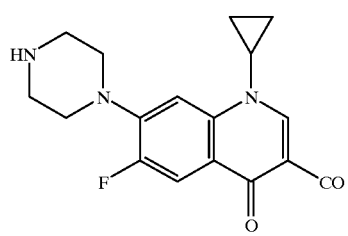
(LXVI)
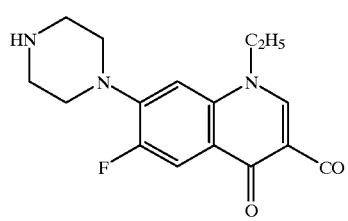
(CCC)
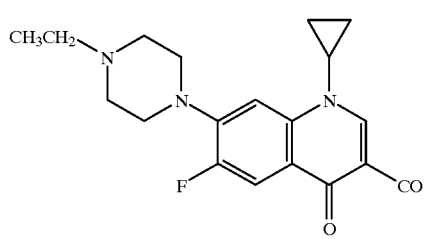
(LXVIII)
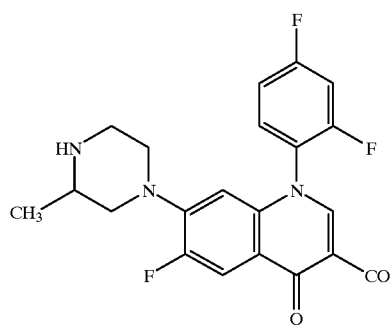
(LXX)
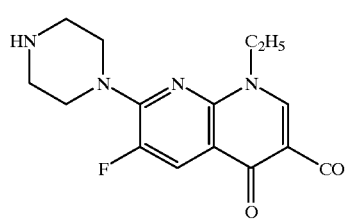
(LXXII)
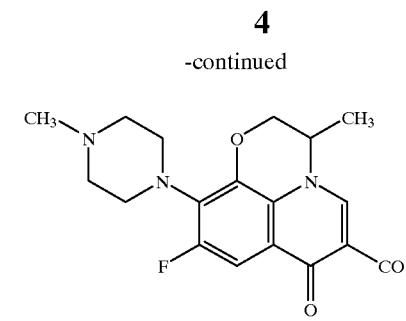
(LXV)
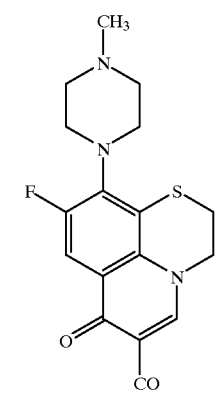
(LXVII)
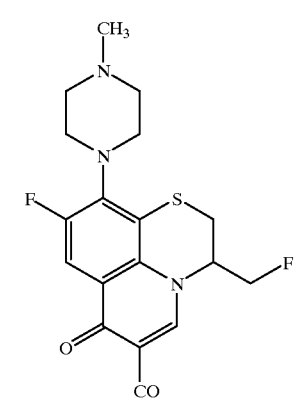
GROUP 8
(CX)
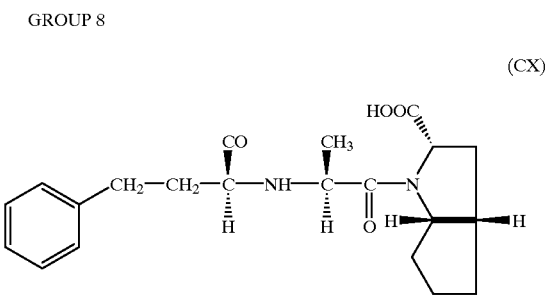
(CIX)
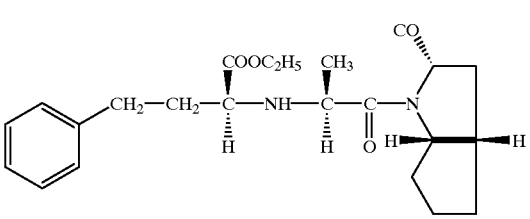

-continued
(CVII)
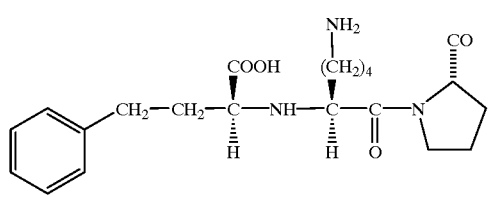
(CVI)
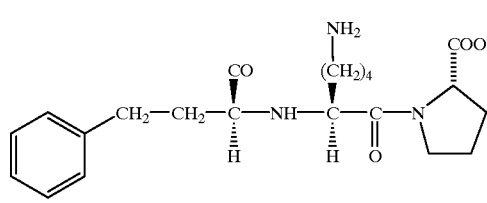
(CXII)
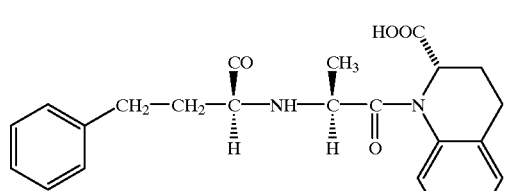
(CXI)
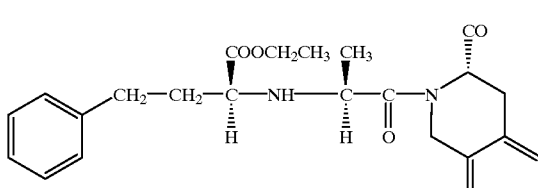
(CI)
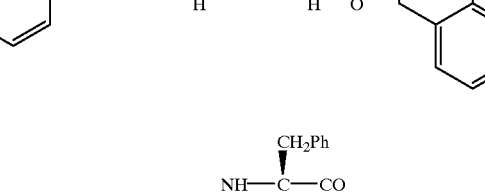
(CII)
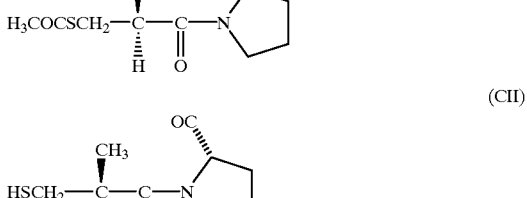
(CIV)
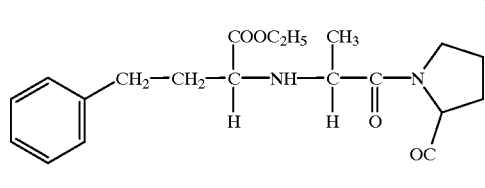
-continued
(CV)
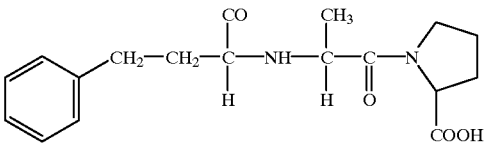
GROUP 15
(XLIV)
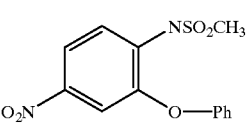
(XXXIV)
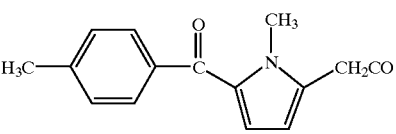
(XXXV)
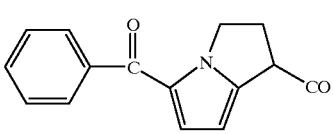
(XXXIII)
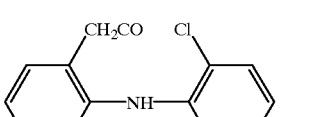
(XXXVII)
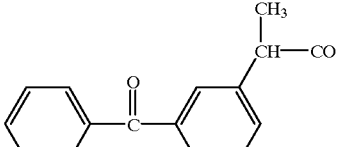
(XXXVI)
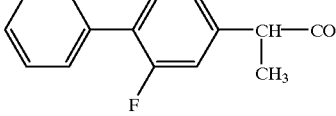
(XXXVIII)
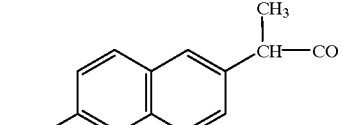
(XXXIX)
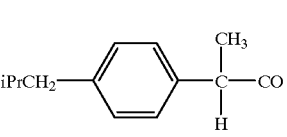

-continued (XLII) 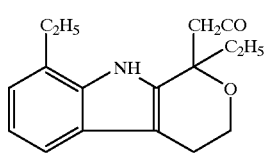

(XLI) 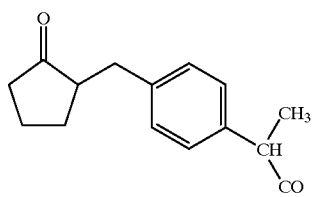

(XLIII) 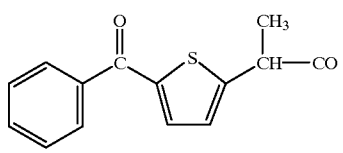

(CCCC) 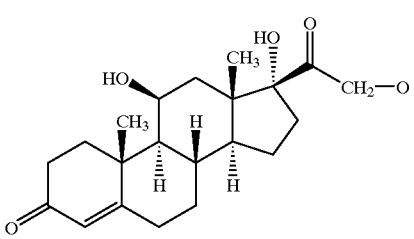

(CCCCI) 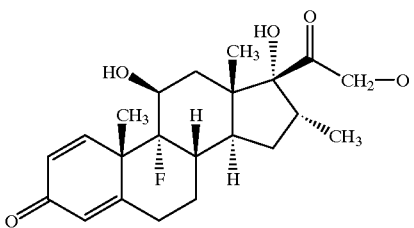

(CCCCII) 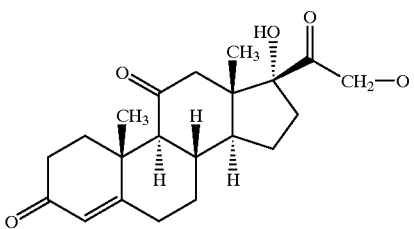

(CCCCIV) 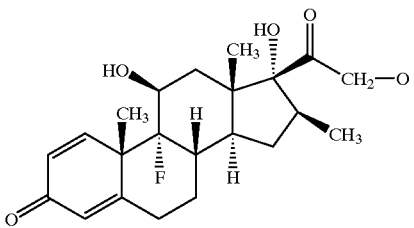

-continued (CCCCIII) 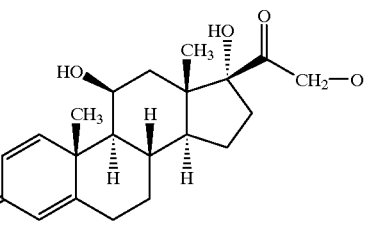

GROUP 16

(XCVII) 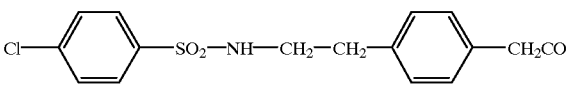

(XCVIII) 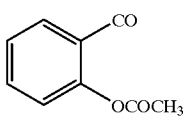

(C) 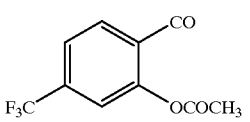

(XCIX) 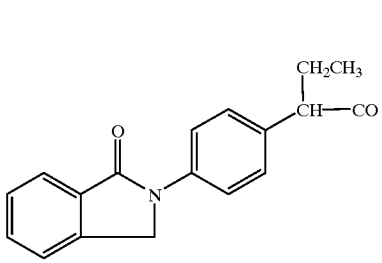

According to this invention, said X having a "bidentate" molecular structure, suitable to interconnect said M according to the general formula (I) is chosen among:

saturated, unsaturated, linear, branched or cyclic, substituted or unsubstituted alkyl chain;

substituded or unsubstituted arylidenic benzenoid, naphthalenic, heteroaromatic pyridinic, pyrimidinic, pyrazolic, pyrazinic, imidazolic, benzimidazolic system;

arylaliphatic system in which the first of said functional groups A and B is on the aromatic portion and the second of said functional groups A and B is on the aliphatic portion, said aromatic portion being constituted by a substituted or unsubstituted benzenoid or heteroaromatic system and said aliphatic portion being constituted by a saturated or unsaturated, linear or branched, substituted or unsubstituted alkylidenic group;

$$-(CH_2)_m-Z-(CH_2)_n- \quad (CXLI)$$

where m,n=1–3, with m=n or m≠n

Z=O, substituted or unsubstituted benzenoidic or heteroaromatic ring

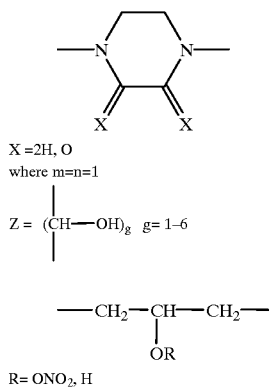

X =2H, O
where m=n=1

Z = (CH—OH)$_g$ g= 1–6

(CXXXVIII)

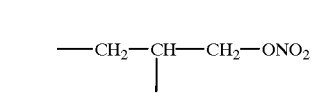

R= ONO$_2$, H (CXXXIX)

—CH$_2$—CH—CH$_2$—ONO$_2$ (XCV)

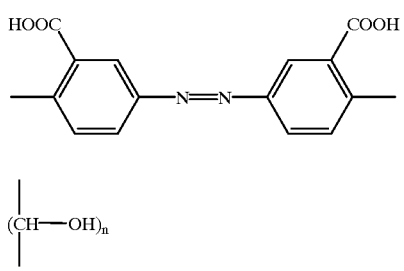

X=O,S

Y(CH$_2$CH$_2$)$_2$ (XCVI)

Y=S, S—S, (OCH$_2$CH$_2$O)$_n$ n=1–5,
R—N where R is chosen among: substituted or unsubstituted, linear, branched alkyl, substituted or unsubstituted aryl (CXLVIII)

HOOC ... COOH
—N=N—

(CXLIII)

(CH—OH)$_n$

Said functional groups indicated by A and B which allow said interconnection between said M and said X are chosen, always according to this invention, among: —O, S, N—R, C=N—R, CO, C(=N—R)—NH, where R is chosen among hydrogen, cyclic, branched, linear alkyl group.

Particularly, when the M unit is chosen as (XLIV), the free valence is saturated with the hydrogen atom; when the M unit is chosen as (CX), (CXII), (CV) the free valence is saturated with the OEt group; in all the other cases the free valence is saturated with the OH group. Still, when said M is chosen as (XLIV), said functional groups A and B are chosen among CO, C(=N—R)—NH, C=N—R, while in all the other cases A and B are chosen among O, S, N—R.

In fact, it has been observed that the pharmacologically active chemical combination of the general formula (I) does not constitute the active principle as such, but undergoes a conversion in the bioactive units corresponding to M; such conversion takes place in different ways and times, according to the treatment conditions, the target or activity site, the administration doses and the pathology ascertained. Therefore, this allows the controlled release of the constituent active principles, and particularly the controlled release of the molecular structures corresponding to M which derive from compounds having a pharmacological activity; such release may happen gradually, for instance when the product corresponding to said chemical combination, obtained according to how M, A, B and X are chosen among the aforementioned ones, has reached the so-called target or active site, allowing in this way to obtain a pharmacological effect which is not only significant, thanks to the release of effective concentrations of active principle, but also long lasting, thanks to the slow release near the action site. In this way, a marked improvement is observed which concerns not only the therapeutical performance but also the toxicological aspects, with ensuing reduction, in many cases, of general and local toxicity.

Besides, the chemical combination represented through the general formula (I) allows in many cases and according to how A and B are chosen to "mask" some functional groups or part of them possibly present on said radicals indicated by M, said functional groups, or part of them, being sometimes responsible for induced adverse reactions that are noticed during the treatment with some drugs whose molecular structure is characterized by the presence of said functional groups. For instance, as is known, the carboxylic function, which is present in the molecular structure of the known non steroidal anti-inflammatory drugs, results to be determinant to direct the molecule towards the inflammatory focus, but also largely responsible for the induced adverse reactions on the gastro-intestinal apparatus. In the case of products of the general formula (I) where M is chosen, for instance, among the units described in group 15, as such function is masked, an improved bioavailability, an improved toxicological profile and a good therapeutical effectiveness are observed.

In particular, a clearly improved gastrointestinal tolerability is obtained relatively to the known anti-inflammatory drugs, while keeping an unchanged effectiveness and demonstrating therefore a reduced gastro-harmfulness. The protracted and controlled release characteristic of the chemical combination according to this invention involves, as said above, also important cynetic advantages, and allows to use said combination in chronic pathologies requiring pharmacological treatments protracted in the time, without incurring the side effects that affect the kidneys and the liver, caused by massive pharmacological treatments protracted in the time.

Always according to this invention, the chemical combination of general formula, (I) has chemical-physical and biochemical characteristics such as to ensure in most cases a good oral absorption and a protracted permanence in the circle, with ensuing considerable advantages, not only therapeutical, but also of administration Always according to this invention, when said X structure suitable to interconnect, through said A and B, said M units, is chosen equal to

Y(CH$_2$CH$_2$)$_2$ (XCVI)

where Y is equal to (OCH$_2$CH$_2$O)$_2$
said structure, depending on the conditions and once the release of M units has taken place according to the above description, can exert a high anti-ischemic activity, thanks to the remarkable vasoactive properties that characterize some aliphatic glycols from which said X has been derived; said anti-ischemic activity, accompanied by a very low toxicity, has to be considered, depending on how M, A and B are chosen, as additional and complementary to the main pharmacological activity for which the combination is used, with ensuing increase of the global pharmacological effect, without any increase in the administered doses.

Besides, when said X is chosen equal to —(CH$_2$)$_7$—, said A and B are chosen equal to CO, the fragment corresponds to the azelaic acid and has itself antibacterial and anti-inflammatory properties and may be advantageously used; in the interconnection of suitable M units, so as to develop a synergical effect.

Always according to this invention, said X, such as for instance a benzenoid arylidenic system, when associated to suitable A and B chosen equal to O, gives rise to fragments corresponding to products having anti-oxidant properties, such as, for instance:

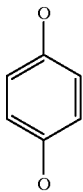

(XCVI)

(residue deriving from the structure of hydroquinone), or having anti-inflammatory properties when X is chosen equal to (CXLVIII), such as, for instance:

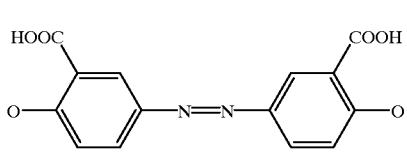

(CXLVIIIa)

(residue deriving from the structure of olsalazine).

Always according to this invention, the products deriving from said pharmacologically active chemical combination of the general formula (I) are also obtainable as pharmacologically acceptable salts according to techniques of known type, in order to improve the characteristics of solubility, chemical-physical and biochemical stability and the administration modalities.

Particularly advantageous, according to this invention, proved to be the preparations of the chemical combination of the general formula (I), realized as described in the following examples, given by way of non limitative indication of the protection scope of the invention.

EXAMPLE 1

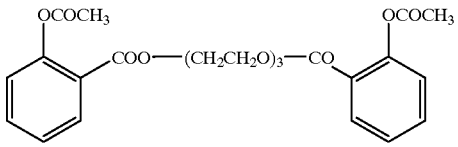

(XIX)

5 g of the chloride of acetylsalicylic acid prepared according to the literature were dropped into a solution constituted by 15 ml of chloroform, 2.07 g of triethylenglycol and 3.87 ml of triethylamine, keeping the temperature at 0° C. The reaction mix was kept under stirring for 1 hour, then 20 ml of H$_2$O were added and the organic phase was separated from the aqueous one.

The solvent was eliminated under reduced pressure, and a dry residue was obtained which was purified by silica gel chromatography, utilizing a mix constituted by methylene chloride/ethyl acetate 1:1 (v/v).

The intermediate fractions were collected, the solvent was evaporated under reduced pressure and 16 g of triethylenglycol bis-acetylsalicylate were obtained (XIX).

IR (cm$^{-1}$): C=O, 1776; 1731 $^1$H-NMR (80 MHz) (ppm) (CDCl$_3$): 2.32 (6H,s); 3.64 (4H,s); 3.72 (4H,m); 4.4 (4H,m); 7.08 (2H,dd); 7.16–7.65 (4H,m); 8.02 (2H,dd).

EXAMPLE 2

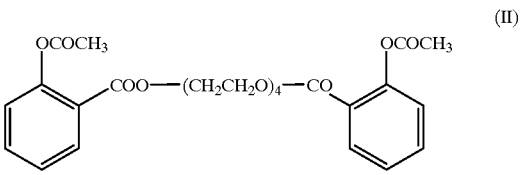

(II)

The compound (II) was prepared according to the procedure described for the synthesis of triethylenglycol bis-acetylsalicylate (XIX), starting from 2 g of the chloride of acetylsalicylic acid, 0.93 g of tetraethylenglycol and 1.5 ml of trietylamine. The product was purified on silica gel chromatography utilizing an eluent mix constituted by methylene chloride/ethyl acetate 1:1 (v/v). The intermediate fractions were collected, the solvent was evaporated under reduced pressure and 0.6 g of tetraethylenglycol bis-acetylsalicylate (II) were obtained.

IR (cm$^{-1}$): C=O, 1776;1731 $^1$H-NMR (80 MHz) (ppm) (CDCl$_3$): 2.25 (6H,s); 3,5 (8H,s); 3.7 (4H,m); 4.32 (4H,m); 7 (2H,dd); 7–7.6 (4H,m); 7.95 (2H,dd). Mass spectrometry (e.i.): M$^+$—CH$_2$=C=O) 476; 294; 250.

EXAMPLE 3

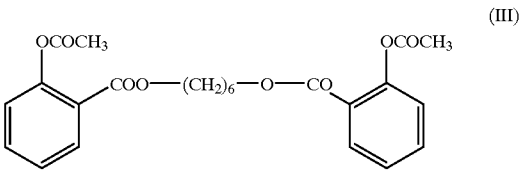

(III)

The compound was prepared according to the procedure described in Example 1 for the synthesis of (XIX), prepared starting from 6 g of the chloride of acetylsalicylic acid, 4.6 ml of TEA and 1.9 g of 1.6-hexandiol. The product was purified by flash chromatography utilizing an eluent mix constituted by ethylether/hexane 7:3 (v/v). The intermediate fractions were collected, the solvent was evaporated under reduced pressure and a solid residue was obtained which, triturated with isopropyl ether, produced 1 g of 1.6-hexandiol bis-acetylsalicylate (II) with m.p.=96° C.

IR (cm$^{-1}$): C=O 1776; 1726 $^1$H-NMR, (80 MHz) (ppm) (CDCl$_3$): 1.55 (4H,s); 1.72 (4H,m); 2.32 (6H,s); 4.28 (4H,t); 7.08 (2H,dd); 7.1–7.68(4H,m); 8(2H,dd).

EXAMPLE 4

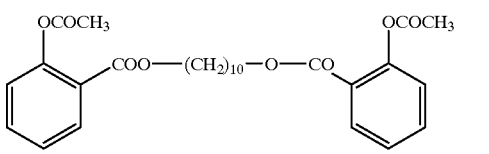
(IV)

The compound (IV) was prepared according to the procedure described in Example 1 for the synthesis of (XIX), starting from 5 g of the chloride of acetylsalicylic acid, 3.5 ml of TEA and 2.17 g of 1.10-decandiol. The product was purified by chromatography utilizing an eluent mix constituted by ethylether/hexane 7:3 (v/v). The intermediate fractions were collected, the solvent was evaporated under reduced pressure and a solid residue was obtained which, trirurated with isopropyl ether, produced 1.37 g of 1.10-decandiol bis-acetylsalicylate (IV) with m.p.=75° C.

IR (cm$^{-1}$): C=O, 1776; 1726 $^1$H-NMR (80 MHz) (ppm) (CDCl$_3$): 1.3 (12H,s); 1.58 (4H,m); 2.3 (6H,s); 4.28 (4H,t); 7.7–65 (6H,m); 8(2H,dd).

EXAMPLE 5

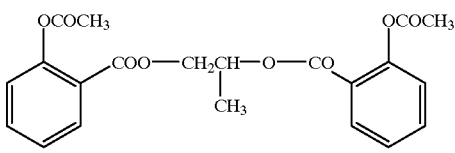
(V)

The compound (V) was prepared according to the procedure described in Example 1 for the synthesis of (XIX), starting from 5,6 g of the chloride of acetylsalicylic acid, 3.8 ml of TEA and 1.06 g of 1.2-propanediol. The product was purified by flash chromatography utilizing an eluent mix constituted by ethylether/hexane 6:4 (v/v). The intermediate fractions were collected, the solvent was evaporated under reduced pressure and 0.55 g of 1.2-propanediol-bis-acetylsalicylate (V) were obtained.

IR (cm$^{-1}$): C=O, 1776; 1731 $^1$H-NMR (80 MHz) (ppm) (CDCl$_3$): 1.22 (3H,d); 2.32 (6H,s); 3.82–4.38 (3H,m); 7–7.7 (6H,m); 7.09 (2H,dd).

EXAMPLE 6

The compound (VI) was prepared according to the procedure described in Example 1 for the synthesis of (XIX), starting from 10 g of the chloride of naproxen, 6.5 ml of TEA and 2.89 g of bis-N-hydroxyethylpiperazne. The product was purified by silica gel chromatography utilizing an eluent mix constituted by methylene chloride/ethyl acetate 1:4 (v/v). The intermediate fractions were collected, the solvent was evaporated under reduced pressure and 3.16 g of an oil were obtained, which, taken up with isopropylether, solidified, producing 1.8 g of 2-N(N'-[2-(6-methoxy-2-naphthyl)]propionyl)piperazinyl)ethyl [2-(6-methoxy-2-naphthyl)]propionate; m.p. 90° C.

$^1$H-NMR (300 MHz) (ppm) (CDCl$_3$): 1.47 (3H,d); 1.54 (3H,d); 1.62–2.44 (6H,m); 3.52 (4H,m); 3.77 (1H,q); 3.83 (1H,q); 3.9 (6H,s); 4.08 (2H,m); 714, (4H,m); 7.3 (2H,m); 7.52 (1H,d); 7.6 (1H,d); 7.68 (4H,m). Mass spectrometry (e.i.): (M$^+$) 554. IR (cm$^{-1}$): NH, 3470, —O—C—O, 1741; NH—C=O 1647.

EXAMPLE 7

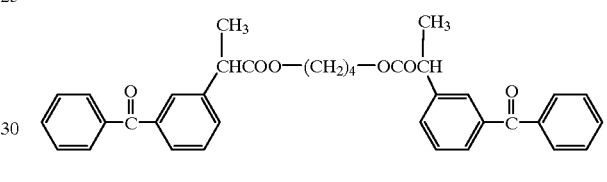
(VII)

11.1 g of ketoprofen were added to a solution of sodium ethoxyde, prepared starting from 1.3 g of sodium metal and 80 ml of ethanol. After the dropping, the mix was kept under stirring for 30' and then the solvent was removed under reduced pressure. The solid residue was taken up with 100 ml of DMF and 0.5 ml of 1,4-dibromobutane. The reaction mix was kept under stirring overnight, then 100 ml of H$_2$O and 100 ml of methylene chloride were added and the organic phase was separated The solvent was eliminated under reduced presure, and a residue was, obtained which was purified by silica gel chromatography, using an eluent mix composed, by ethylether/hexane 4:6 (v/v). The head fractions were collected, the solvent was evaporated under reduced pressure and 7.5 g of 1,4-butandiole bis-2-[(3-benzoyl)phenyl]propionate were obtained.

$^1$H-NMR (80 MHz) (ppm) (CDCl$_3$): 1.49 (6H,d); 1.52 (4H,m); 3.78 (2H,q); 4.02 (4H,m); 7.5 (10H,m); 7.71 (8H, m). Mass spectrometry (e.i.): (M$^+$) 562. IR (cm$^{-1}$): C=O, 1756; —OC=O, 1666.

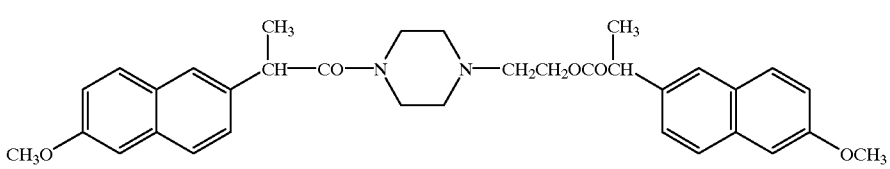
(VI)

EXAMPLE 8

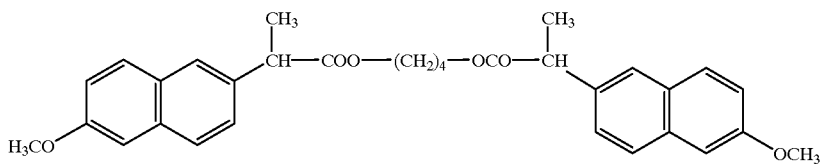

(VIII)

10 g of naproxen were added to a solution of sodium ethoxyde, prepared starting from 1.04 g of sodium metal and 100 ml of EtOH. The reaction mix was kept under stirring for 15' and then the solvent was removed under reduced pressure and the residue was taken up with 100 ml of DMP. 13 ml of 1,4-dibromobutane were added and the reaction mix was elaborated after 12 h, according to the procedure previously described. The residue was purified by silica gel chromatography, using an eluent mix composed by ethylether/hexane 6:4 (v/v). The head fractions were collected, the solvent was evaporated under reduced pressure and 9.5 g of 1,4-butandiole bis-[2-(6-methoxy-2-naphthyl)]propionate (VIII) with m.p. 117° C. were obtained.

$\alpha_D$(CH$_3$CN)=+42.8.°, c=1% $^1$H-NMR (80 MHz) (ppm) (CDCl$_3$): 1.48 (4H,m); 1.52 (6H,d); 3.76 (2H,q); 3.88 (6 H,s); 3.99 (4H,m); 7.1–7.42(6H,m); 7.51–7.74 (6H,m). IR (cm$^{-1}$): C=O, 1724

EXAMPLE 9

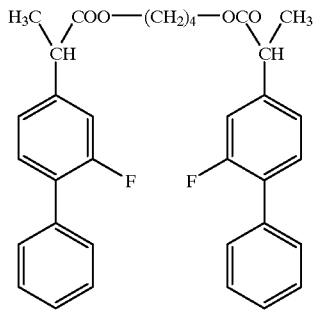

(IX)

10 mg of flurbiprofen were added to a solution of sodium methoxyde, prepared starting from 1 g of sodium metal and 100 ml of methanol. The reaction mix was kept under stirring for 15', then the solvent was removed under reduced pressure and the residue taken up with 100 ml of DMF. 4.75 g of 1,4-dibromobutane were added and the reaction mix was elaborated after 12 h according to the procedure previuosly described. The residue was purified by silica gel chromatography, using an eluent mix constituted by ethylether/hexane 6:4 (v/v). The head fractions were collected the solvent was evaporated under reduced pressure and 10 g of 1,4-butanediole bis[(2-[4-(3-fluoro)biphenylyl] propionate (IX) with m.p: 81° C. were obtained.

$^1$H-NMR (80 MHz) (ppm) (CDCl$_3$): 1.48 (6H,d); 1.6 (4H,m); 3.71 (2H,q); 4.08 (4H,m); 7.06 (2H,m); 7.21 (2H, d); 7.27–7.61 (12H,m). IR (cm$^{-1}$): C=O, 1736.6.

EXAMPLE 10

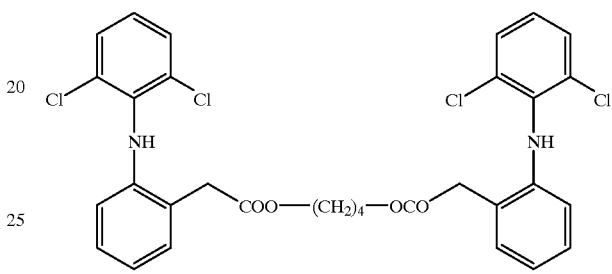

(X)

10 mg of diclofenac were added to a solution of sodium ethoxyde prepared starting from 0.81 g of sodium metal and 80 ml of EtOH. The reaction mix was kept under stirring for 15', then the solvent was removed under reduced pressure and the residue was taken up with 80 ml of DMF. 7.3 g of 1,4-dibromobutane were added and the reaction mix was elaborated after 12 h according to the procedure previously described. The residue was purified by silica gel chromatography, using an eluent mix constituted by ethylether/hexane 6:4 (v/v). The head fractions were collected, the solvent was evaporated under reduced pressure and 9.5 g of 1,4-butandiole bis-[2,6-dichloroanylino) phenyl]acetate (X) with m.p. 115° C. were obtained.

$^1$H-NMR (300 MHz) (ppm) (CDCl$_3$): 1.70 (4H,m); 3.79 (4H,m); 4.14 (4H,m) 6.55 (2H,d); 6.8–7.00 (6H, m and s superimposed); 7.11 (2H,t); 7.20 (2H,d); 7.32 (4H,d). IR (cm$^{-1}$): NH 3294.4; C=O, 1729.2.

EXAMPLE 11

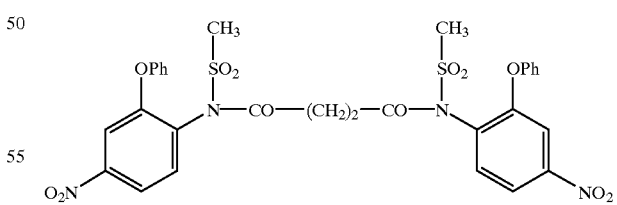

(XI)

The dichloride of succinic acid was dropped into a solution of nimesulide (15 g) and thriethylamine (5 ml) in methylene chloride (100 ml) at 0° C. and under nitrogen atmosphere. The reaction mix was kept under stirring at 0° C. for 5 h and then overnight at room temperature. The solid so formed was recovered by filtration and treated with H$_2$O to remove the triethylamine hydrochloride. Afterwards, it was treated with boiling methylene chloride boiling and the dissolved part was removed by filtration. The solvent was removed under reduced pressure from the filtrate, obtaining a solid which was triturated with in ethyl alcohol. 1.71 g of bis-(N-[(2-phenoxy-4-nitro)phenyl]-N'-methansulfonyl) succinamide were obtained (XI).

$^1$H-NMR (300 MHz) (ppm) (DMSO): 3.41 (s,4H); 3.51 (s,6H); 7.2 (d,2H); 7.36 (t,2H); 7.52 (m,8H); 7.93 (d,2H); 8.1 (dd,2H). Mass spectrometry (e.i.); M$^+$ absent; 391 M$^+$-nimesulide radical.

EXAMPLE 12

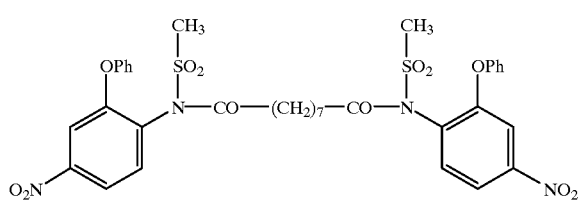

(XII)

The dichloride of azelaic acid was dropped into a solution of nimesulide (15 g) and trietylamine (35 ml) in methylene chloride (150 ml) at 0° C. under nitrogen atmosphere. The reaction mix was kept under stirring at 0° C. for 2 h and 50 ml of chloroform were added to dissolve the solid so formed. The solution was washed with a 5% solution of potassium hydroxyde and then the solvent was removed under reduced pressure and an oily yellow residue was obtained which was purified utilizing an eluent mix constituted by toluene/ethyl acetate 9:1 (v/v). The intermediate fractions were collected, the solvent evaporated under reduced pressure, obtaining an oil which, treated with methanol, solidified. 9.15 g of bis-N-[(2-phenoxy-4-nitro)phenyl]-N'-methanesulfonyl) azelamide with m.p.=165° C. were obtained (XII).

$^1$H-NMR (300 MHz) (ppm) (DMSO); 1.34 (s,6H); 1.6 (4H,m); 2.2 (4H,t); 7.08 (4H,d); 7.3 (2H,t); 7.37 (2H,s); 7.48 (2H,t); 7.6 (2H,d); 7.68 (2H,d); 8.01 (2H,dd). Mass spectrometry (e.i.); M$^+$ absent; 461 M$^+$-nimesulide radical.

EXAMPLE 13

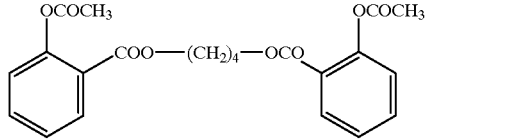

(XIII)

Acetylsalicylic acid (10 g) dissolved in DMF (50 ml) was dropped into a suspension of sodium hydride (1.8 g) in DMF (20 ml). After the addition, the reaction mix was kept under string for 30 minutes to complete the formation of the sodium salt. 1,4-dibromobutane (6.1 g) was dropped into the reaction mix and the reaction mix was kept under stirring overnight. Water (100 ml) and methylene chloride (100 ml) were added and the organic phase was separated, dried and the solvent was removed under reduced pressure. The solid residue was purified by crystallization from isopropyl alcohol, obtaining 15 g of 1,4-buthanediol bis-acetylsalycylate (XIII) with m.p. 124° C.

$^1$H-NMR (80 MHz) (ppm) (CDCl$_3$): 1.86 (4H,m); 2.32 (6H,s); 4.3 (4H,m); 6.98–7.72 (6H,m); 8.00 (2H,dd). IR (cm$^{-1}$): CF=O, 1756; O—C=O 1729. Mass spectrometry (e.i.); (M$^+$—CH$_2$=C=O)372.

EXAMPLE 14

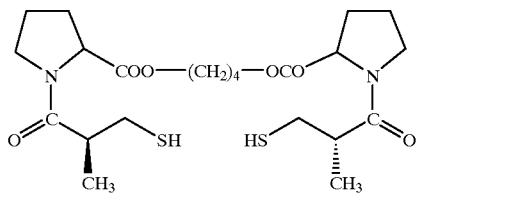

(XIV)

80% sodium hydride (0.66 g) was added portionwise, under in nitrogen atmosphere, to a solution of captopril (5.04 g) in anhydrous DMF (30 ml). After the addition, the reaction mix was kept under stirring for 30 minutes and 1,4-dibromobutane (2.5 g) was added. After 8 days the solvent was removed under reduced pressure from the reaction mix, the residue was treated with a 5% solution of sodium hydrogen carbonate (30 ml) and ethyl acetate (50 ml), The solvent was removed under reduced pressure from the organic phase and the residue was purified by silica gel chromatography, utilizing an eluent mix constituted by toluene/ethyl, acetate/acetic acid 8:1:1 (v/v/v). The intermediate fractions were collected, the solvent was evaporated under reduced pressure and 0.5g of 1,4-butandiol bis-N-(S)[(3-mercapto-2-methyl)propionyl]-L-prolinate (XIV) were obtained.

IR (cm$^{-1}$): SH 2550; O—CO— 1747, —CON— 1642. $^1$H-NMR (300 MHz) (ppm) (CDCl$_3$): 1.12 (6H,d); 1.5 (2SH,s); 1.62 (4H,m); 2.06 (8H,m); 2.36 (2H,m); 2.77 (4H,m); 3.6 (4H,m); 4.08 (4H,m); 4.45 (2H,m). Mass spectrometry (e.i.): (M$^+$) 488; (M$^+$—SH) 455.

EXAMPLE 15

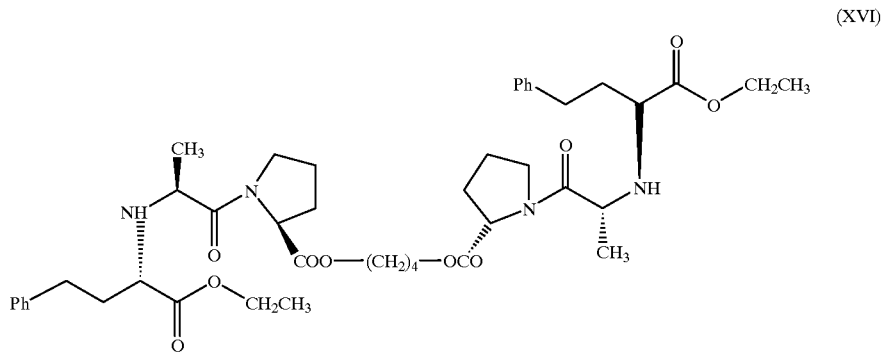

(XVI)

80% sodium hydride (0.3 g) was added portionwise and under stirring to a solution of enalapril (4.32 g) in DMF (15 ml). A solution of 1,4-dibromobutane (1.11 g) in DMF (5 ml) was added and the reaction mix was kept under stirring for 3 days. The solvent was removed under reduced pressure and the residue was treated with ethyl ether. The solid was removed by filtration and the filtrate was purified by silica gel chromatography, utilizing an eluent constituted by heptane/chloroform/ethanol 7.5:0.5:2. (v/v/v). The intermediate fractions were collected, the solvent was evaporated under reduced pressure and 1.88 g of 1,4-butanediol bis-N-(S)-[1-carbetoxy-3-phenylpropionyl]-L-alanyl]-L-prolinate (XVI) were obtained.

$^1$H-NMR (306 MHz) (ppm) (CDCl$_3$): 1.23 (20H,m); 2.09 (8H,m); 2.67 (4H,m); 3.52 (6H,m); 4.12 (12H,m); 4.5 (2H,m); 7.18 (6H,m); 7.27 (4H,m).

EXAMPLE 16

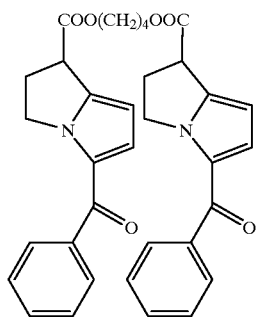
(XXVI)

Ketorolac (2.3 g) dissolved in DMF (35 ml) was dropped under stirring into a suspension of 80% sodium hydride (0.32 g). The reaction mix was kept under stirring for 30 minutes at 40° C. 1 ml of 1,4-dibromobutane (1 ml) was added and the reaction mix was kept under stirring overnight at room temperature. The solvent was removed under reduced pressure and the residue was treated with H$_2$O and methylene chloride. The organic phase was separated, dried on sodium sulfate and a residue was obtained which was purified by silica gel chromatography, utilizing an eluent mix constituted by ether/petroleum ether 4:6 (v/v). The intermediate fractions were collected, the solvent was evaporated under reduced pressure and 1.3 g of (XXVI) were obtained.

$^1$H-NMR (80 MHz) (CDCl$_3$) (ppm): 1.83 (8H,m); 2.81 (4H,m); 4.13 (4H,t); 4.49 (2H,m); 6.04 (2H,d); 2.77 (4H,m); 6.78 (2H,d); 7.41 (6H,m); 7.74 (4H,m).

EXAMPLE 17

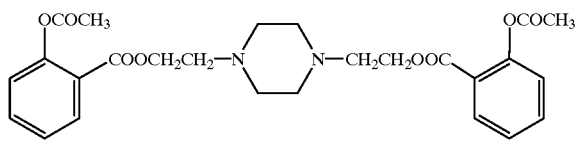
(XVII)

A suspension of acetylsalicylic acid chloride (4.5 g) and 1,4-bis(2-hydroxyethyl)piperazine (1.98 g) in methylene chloride (20 ml) was kept under siring overnight at room temperature. The solid so formed was recovered by filtration; the free base was obtained by treatment with sodium hydrogen carbonate, extracted with methylene chloride and dried on sodium sulfate. The solvent was removed under reduced pressure and the residue purified by silica gel chromatography, utilizing an eluent mix chloroform/methanol 98:1 (v/v). The central fractions were collected, the solvent was evaporated under reduced pressure and 2.5 g of 1,4-bis[2-(salyciloyloxy)ethyl]piperazine were obtained.

$^1$H-NMR (80 MHz) (CDCl$_3$) (ppm): 2.3 (6H,s); 2.55 (8H,s); 2.71 (4H,t); 4.35 (4H,t); 7.32 (6H,m); 7.97 (2H,dd).

EXAMPLE 18

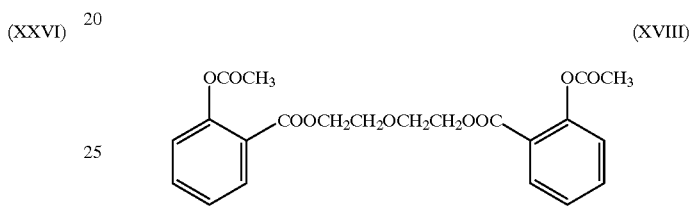
(XVIII)

A solution of acetylsalicylic acid (5.64 g) in DMF (20 ml) was added under stirring to a suspension of 80% NaH (0.98 g). The reacxtion mix was kept under stirring at 40° C.; 2,2'-dibromo-diethylether (5 g) was added at room temperature and the reaction mix was kept under stirring for 3 days. The solvent was removed under reduced pressure and the residue was treated with H$_2$O and methylene chloride. The organic phase was separated, dried on magnesium sulphate and the solvent removed under reduced pressure. The residue was purified by silica gel chromatography, utilizing an eluent mix toluene/ethyl acetate 85.15 (v/v). The solved was removed from the tail fractions under reduced pressure and 2.3 g of diethyleneglycol bis-acetylsalycilate were obtained with m.p.=85° C.

$^1$H-NMR (80 MHz) (CDCl$_3$) (ppm): 2.32 (6H,s); 3.79 (4H,m); 4.42 (4H,m); 7.18 (4H,m); 7.52 (2H,m); 8.0 (2H,dd).

EXAMPLE 19

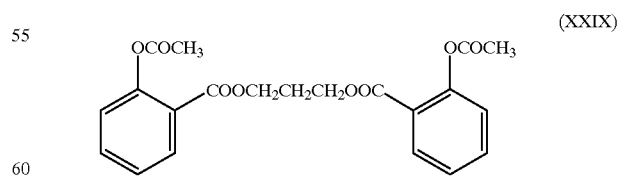
(XXIX)

Acetylsalicylic acid (10 g) dissolved in DMF (50 ml) was dropped into a suspension of sodium hydride (1.8 g) in DMF (50 ml). After the addition, the reaction mix was kept under stirring for 30 minutes to complete the formation of the sodium salt. 1,3-dibromopropane (5.7 g) was dropped into the reaction mix and the reaction mix was kept under stirring overnight. H₂O (100 ml) and methylene chloride (100 ml) were added and the organic phase was separated, dried and the solvent was removed under reduced pressure. The solid residue was purified by chromatography, utilizing an eluent mix constituted by ethyl ether/petroleum ether 3:7 (v/v). The intermediate fractions were collected, the solvent was evaporated under reduced pressure and a solid was obtained which was triturated with isopropylether. 3 g of 1,3-propanediol bis-acetylsalycylate with m.p. 63° C. were obtained.

¹H-NMR (80 MHz) (ppm) (CDCl₃): 2.19 (2H,t); 2.32 (6H,s); 4.43 (4H,t); 7.0–7.66 (6H,m); 7.99 (2H,dd).

EXAMPLE 20

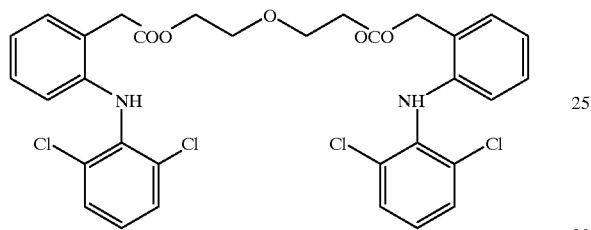
(CVIII)

A solution of the, sodium salt of diclofenac (13.3 g) in DMF (25 ml) was added to a solution of 2,2'-dibromo-diethylether (12.3 g) in DMF (15 ml) kept at room temperature and under nitrogen flow. The reaction mix was left to react for 2 days and the solvent was removed under reduced pressure. The residue was taken up with ethyl acetate, washed first, with a saturated solution of potassium carbonate and then with H₂O. The organic phase was separated, dried and the solvent removed under reduced pressure. The residue was purified by silica gel chromatography, utilizing an eluent mix toluene/ethyl acetate 98:2 (v/v). The head fractions were collected, the solvent removed under reduced pressure and 1.3 g of diethylenglycol bis-[2-(2,6-dichloroanylino)phenyl] acetate were obtained.

¹H-NMR (80 MHz) (CDCl₃) (ppm): 3.67 (4H,m); 3.31 (4H,s); 4.25 (4H,m); 6.53 (2H,d); 6.89 (2NH,s, exchangeable with D₂O); 6.95 (4H,m); 7.1 (2H,t); 7.31 (4H,d).

EXAMPLE 21

Hydroquinone (0.61 g) was added to a solution of TEA (0.8 g) in ethyl ether (25 ml); naproxene chloride dissolved in ethylether (35 ml) was dropped into the salt so formed. The reaction mix was kept under stirring overnight, diluted with H₂O, neutralized with a saturated solution of sodium carbonate and, extracted with ethylether; the solvent was removed under reduced pressure and a residue was obtained which was triturated with isopropyl ether and crystallized from an isopropylether/toluene mix 93:5 (v/v). 0.8 g of hydroquinone bis[2-(6-methoxy-2-naphtyl)]propionate were obtained. m.p. 153° C.

¹H-NMR (80 MHz) (ppm); 1.68 (6H,d); 3.91 (6H,s); 4.05 (2H,q); 6.92 (4H,s); 7.17 (4H,m); 7.43 (2H,m); 7.79 (6H,m). Elemental analysis:

calc. C=76.39% H=5.66%
found C=76.64% H=5.51%

EXAMPLE 22

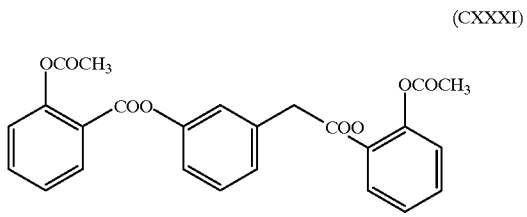
(CXXXI)

A solution od acetylsalyciloylchloride (24 g) in acetonitrile (80 ml) was dropped slowly and under stirring into a solution of 3-hydroxybenzyl alcohol. The reaction mix was kept under stirring overnight, the triethylamine hydrochloride was removed by filtration and the solvent was evaporated from the filtrate under reduced pressure. The residue was crystallized by isopropanol and 3.5 g of 3-hydroxybenzyl alcohol bis-acetylsalicylate were obtained. m.p.: 125–127° C.

¹H-NMR (80MHz) (ppm): 2.18 (3H,s); 2.29 (3H,s); 5.3 (2H,s); 7.34 (10H,m); 8.12 (2H,m). EXAMPLE 23

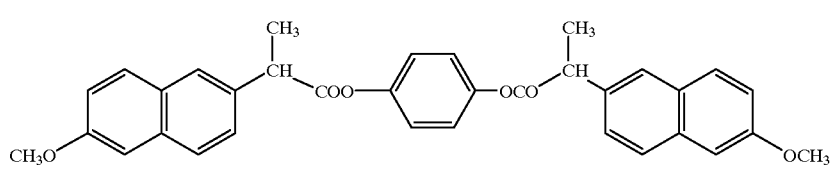
(CXXX)

EXAMPLE 23

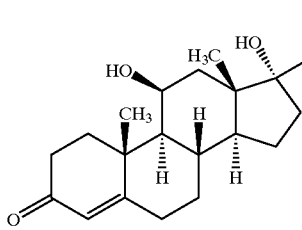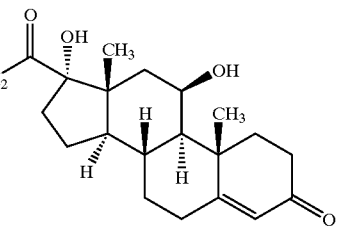

(CCCCV)

Azelaic acid dichloride (0.31 g) was dropped into a solution of hydrocortisone (1 g) in pyridine (5 ml). The reaction mix was kept under stirring overnight, treated with a 5% hydrocloric acid solution and extracted with chloroform. The organic layer was washed with a 5% hydrogen carbonate solution, dried and evaporated to dryness. The residue was purified by silica gel chromatography, utilizing an eluente mix chloroform/methanol 9.5:0.5 (v/v). The central fractions were collected, the solvent was removed under reduced pressure and 0.75 g of di(21-hydrocortisone)azelate were obtained.

$^1$H-NMR (300 Mhz) (DMSO) (ppm): 0.75 (6H,s); 0.94 (6H,m); 1.29 (6H,m); 1.38 (6H,s); 1.55 (4H,t); 1.62 (4H,d); 1.78 (2H,m); 1.91 (4H,d); 2.08 (2H,d); 2.13 (6H,m); 2.38 (4H,t); 2.49 (8H,s); 3.18 (2H,d); 4.23 (2H,broad s); 4.36 (2H,d); 4.72 (2H,d); 5.05 (2H,d); 5.4 (2H,d); 5.57 (2H,d). Mass spectrometry (e.i.): ($M^+$) 876

Some biological characteristics of the above described products have been determined; in particular, acute toxicity was approximately evaluated by oral administration of one dose of substance to batches of 10 mice. The incidence of lethality and the onset of toxic symptomatology were registered for an observation period of 14 days. Even upon administration of a dose of 100 mg/kg the animals showed no signs of toxicity.

In addition, the test compound have been administred at doses of 30 mg/kg of di(21-hydrocortisone) azelate (CCCCV) for three days, as compared to the native agents.

Differently from these latter test compounds have been excellently tolerated, without provoking any apparent toxicity in treated animals. Besides; also the anti-inflammatory activity and the gastrointestinal tolerability of the following chemical combinations according to this invention were determined:

(VIII)
(X)
(XI)
(IX)
(VII)
(CVIII)

The anti-inflammatory activity was determined according to the method of carrageen edema, as described by WINTER et al. Proc.Soc.Exp.Biol.Med. 111,544 (1962), in the rat.

The gastrointestinal tolerability was evaluated by oral administration in the rat.

The anti-arthritic activity of (CCCCV) was determined in the rat, according to the standard adjuvant arthritis method, consisting in the injection of a suspension killed Mycobacterium butyricum in mineral oil in the right hind paw under light ether anesthesia. The volume of the left hindpaw was measured by plethysmography. All the test substances, that were suspended in carboxymethylcellulose 0.5–2% and administred intraperitoneally, resulted to be effective in inhibiting significantly the Mycobacterium butyricum induced paw volume increase in a dose related way, with a potency comparable with the parent compound and a peak time effect and a greater duration of pharmacological activity.

The results are shown in Table 1, which summarizes the study of the anti-inflammatory properties of the compounds under examination after oral administration.

TABLE 1

The activities specified in the following have been expressed as power ratio related to the basic product, taken as unit standard.

| COMPOUND | ANTIEDEMIGENIC ACTIVITY | GASTROINT. TOLERABILITY |
|---|---|---|
| (VIII) | | |
| Naproxen | 1 | 1 |
| (CVIII) | 0.8 | 0.2 |
| (X) | 0.8 | 0.1 |
| Diclofenac | 1 | 1 |
| (XI) | 1.0 | 0.8 |
| Nimesulide | 1 | 1 |
| (IX) | 0.8 | 0.3 |
| Flurbiprofen | 1 | 1 |
| (VII) | 0.9 | 0.3 |
| Ketoprofen | 1 | 1 |

In addition, the gastrointestinal tolerability was examined in (CCCCV), as compared to the native agent. Always the test compound following intraperitoneal administration, was shown to be significantly better tolerated than the parent compound.

Always according to this invention, biological tests have been carried out suitable to determine the anti-hypertension activity of the following compounds:

(XVI)
(XIV)

The anti-hypertension activity was determined according to the angiotensine I hypertension method, as described by LAUBIE et al. J.Cardiovasc.Pharmacol. 6,1076 (1984) in the rat.

After endoperitoneal administration, the products under examination resulted to be all effective in inhibiting the hypertension effect induced by angiotensine I, with a power comparable to the basic substance taken as reference, and showed a peak time and a duration of the pharmacological activity significantly greater.

There were determined experimentally the platelet anti-aggregating activity and the gastrointestinal tolerability of the following products, according to this invention:

(XIII)
(XVII)
(XVIII)
(III)

The platelet anti-aggregating activity was evaluated in vivo on the collagen-stimulated platelets, according to the method described by PINON, J.Pharmacol.Methods 12,79 (1984); the gastrointestinal tolerability was evaluated by oral administration in the rat.

The results are shown in Table 2, which summarizes the study of the antithrombotic properties of said products (III), (XIII) (XVII) and (XVIII) after their oral administration.

TABLE 2

The platelet anti-aggregating activity has been expressed as power ratio related to the basic product, taken as unit standard.

| COMPOUND | PLATELET ANTI-AGGREGATING ACTIVITY | GASTROINT. TOLERABIL. |
| --- | --- | --- |
| (XIII) | 0.8 | 0.1 |
| (III) | 0.8 | 0.1 |
| (XVII) | 0.7 | 0.2 |
| (XVIII) | 0.8 | 0.2 |
| Aspirin | 1 | 1 |

For the products IX, X and (CCCCV) the plasmatic concentration after oral administration of the products in the rats was evaluated comparatively to the native products.

Since the first hours of administration of IX, XI and (CCCCV), significant quantities of the native products were found.

The time of plasmatic elimination half-life observed in the animals treated with IX, XI and (CCCCV), resulted to be significantly higher, sometimes even by 300%, than the values corresponding to the native compounds.

What is claimed is:
1. A compound of formula (I): M—A—X—B—M (I)

wherein each M is

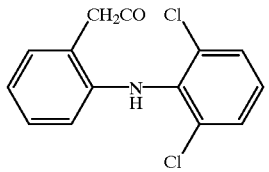

(XXXIII)

X is —$(CH_2)_{1-4}$—; and

A and B are both oxygen.

2. The compound of formula (I) according to claim 1, which is

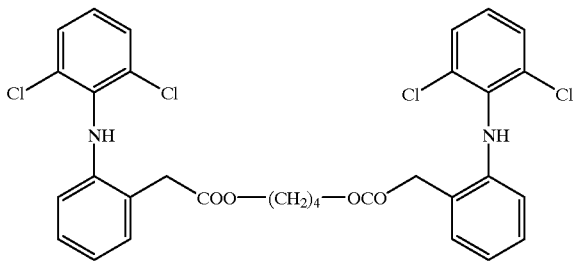

(X)

* * * * *

UNITED STATES PATENT AND TRADEMARK OFFICE
CERTIFICATE OF CORRECTION

PATENT NO. : 6,369,260 B1  Page 1 of 1
DATED : April 9, 2002
INVENTOR(S) : Sannicolo et al.

It is certified that error appears in the above-identified patent and that said Letters Patent is hereby corrected as shown below:

<u>Title page,</u>
Item [73], the name of the assignee correctly should read:
-- Laboratori Alchemia S.r.l. --.
The name of the second assignee remains the same.

Signed and Sealed this

Twenty-fourth Day of September, 2002

Attest:

Attesting Officer

JAMES E. ROGAN
*Director of the United States Patent and Trademark Office*